(12) United States Patent
Hainfeld

(10) Patent No.: US 6,645,464 B1
(45) Date of Patent: *Nov. 11, 2003

(54) LOADING METAL PARTICLES INTO CELL MEMBRANE VESICLES AND METAL PARTICULAR USE FOR IMAGING AND THERAPY

(76) Inventor: James F. Hainfeld, 44 Bradley Dr., Shoreham, NY (US) 11786

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/363,204

(22) Filed: Jul. 29, 1999

Related U.S. Application Data

(60) Provisional application No. 60/094,669, filed on Jul. 30, 1998.

(51) Int. Cl.$^7$ .......................... C12N 13/00; A61K 51/00
(52) U.S. Cl. ................... 424/1.29; 424/1.29; 424/1.17; 424/1.11; 424/1.65; 424/9.3; 424/9.32; 424/9.321; 424/9.323; 435/173.6; 435/173.4; 435/173.5; 435/285.2; 435/2
(58) Field of Search .............................. 424/1.17, 1.29, 424/1.11, 1.65, 9.3, 9.32, 9.321, 9.323; 435/173.6, 173.4, 173.5, 285.2, 2

(56) References Cited

U.S. PATENT DOCUMENTS

| | | | |
|---|---|---|---|
| 4,269,826 A | | 5/1981 | Zimmermann et al. |
| 4,652,449 A | | 3/1987 | Ropars et al. |
| 4,839,111 A | * | 6/1989 | Huang .......................... 264/4.6 |
| 4,935,223 A | | 6/1990 | Phillips |
| 5,163,896 A | * | 11/1992 | Suthanthiran et al. .......... 600/1 |
| 5,292,524 A | * | 3/1994 | Male et al. ................. 424/1.17 |
| 5,360,895 A | * | 11/1994 | Hainfeld et al. .......... 530/391.5 |
| 5,542,935 A | * | 8/1996 | Unger et al. ................. 604/190 |
| 5,612,207 A | * | 3/1997 | Nicolau et al. ........... 435/173.6 |
| 5,688,486 A | * | 11/1997 | Watson et al. .............. 424/1.65 |
| 5,690,903 A | * | 11/1997 | Hainfeld .................... 424/1.49 |
| 5,948,384 A | * | 9/1999 | Filler ........................ 424/1.29 |
| 6,001,054 A | * | 12/1999 | Regulla et al. ................. 600/1 |

OTHER PUBLICATIONS

Mian, T.A. et al., Backscatter radiation at bone–titanium interface from high–energy x and gamma rays, Int. J. Radiation Oncol. Biol. Phys., 13, pp. 1943–1947, 1987.

Huq, M.S. et al., The effect on dose of kilovoltage x–rays backscattered from lead, Int. J. Radiation Oncol. Biol. Phys., 24, pp. 171–175, 1992.

Verhaegen, F. And Seuntjens, J., Monte Carlo study of electron spectra and dose from backscattered radiation in the vicinity of media interfaces for monenergtic photons of 50–1250 keV, Radiation Res., 143, pp. 334–342, 1995.

Gagnon, W.F. et al., Dose enhancement from backscattered radiation at tissue–metal interfaces irradiated with high energy electrons, British J. Radiology, 53, pp. 466–470, 1980.

Das, I.J. amd Kahn, F.M., Backscatter dose perturbation at high atomic number interfaces in magavoltage photon beams, Med. Phys., 16, pp. 367–375, 1989.

Johnson DH. Phase III trial (E5592) comparing cisplatin plus etoposide with cisplatin plus paclitaxel at two dose levels for treatment of advanced non–small–cell lung cancer. Eastern Cooperative Onocology Group. J Natl Cancer Inst Monogr. 1995;(19):61–3.

Baselga J, et al. Phase II study of weekly intravenous recombinant humanized anti–p185HER2 monoclonal antibody in patients with HER2/neu–overexpressing metastaic breast cancer. J Clin Oncol. Mar. 1996; 14(3):737–44.

Hung MC, et al. HER–2/neu–targeting gene therapy—a review. Gene. Jun. 14, 1995; 159(1):65–71.

Yan DH. Targeting human breast cancer cells that overexpress HER–2/neu mRNA by an antisense iron responsive element. Biochem Biophys Res Commun. May 1998; 246(2):353–8

Fidler IJ, et al. Molecular determinants of angiogenesis in cancer metastasis. Cancer J Sci Am. 1998 May 1998;4 Suppl 1:S58–66.

Presta LG, et al. Humanization of an anti–vascular endotheial growth factor monoclonal antibody for the therapy of solid tumors and other disorders. Cancer Res. Oct. 15, 1997;57(20):4593–9.

Boehm T, et al. Antiangiogenic therapy of experimental cancer does not induce acquired drug resistance. Nature. Nov. 27, 1997;390(6658):404–7.

Dass CR, et al. Enhanced anticancer therapy mediated by specialized liposomes. J. Pharm. Pharmacol. Oct. 1997;49(10):972–5.

Gahbauer R, et al. Boron neutron capture therapy: principles and potential. Recent Results Caner Res. 1998;150:183–209. Abstract Only Provided.

(List continued on next page.)

*Primary Examiner*—Russell Travers
*Assistant Examiner*—Shahnam J Sharareh
(74) *Attorney, Agent, or Firm*—Pierce Atwood; Kevin M. Farrell

(57) ABSTRACT

Delivery of metal particles to living tissue, then applying external energy that interacts with the metal particles, is found to selectively increase the energy deposition and interaction surrounding the metal particles. The method is useful to improve treatment of various conditions, since targeted cells may be selectively altered or killed. Metal particles are also loaded into cells or membrane vesicles by placing metal seed particles into the cells or vesicles, then chemically depositing additional metal on the metal seed particles. The metal particles are useful to improve imaging and therapies by their interaction with externally applied energy.

43 Claims, No Drawings

OTHER PUBLICATIONS

Faivre–Chauvet A, et al. Pre–clinical and clinical studies of two new bifuntional chelating agents for immunoscintigraphy with 111In–anti–CEA monoclonal antiboby. Nucl Med Commun. Sep. 1996:17(9):781–9.

McNamara DA, et al. Significance of angiogenesis in cancer therapy. Br J Surg. Aug. 1998;85(8):1044–55.

Huang X, et al. Tumor infarction in mice by antibody–directed targeting factor to tumor vasculature. Science. Jun. 24, 1997;275(5299):547–50.

Calabrese LC, et al. Arterial imaging. Curr Opin Cardiol. Oct. 1992;7(5):843–50.

Handley, D. A. (1989), in Hayat, M. A. (Ed.), colloidal Gold: Principles, Methods, and Applications. vol. 1, pp. 1–32, Academic Press, San Diego, CA.

De Harven E, et al. Antibody drug carrier for immunotherapy of superficial baldder cancer: ultrastructural studies. Cancer Res. Jun. 1, 1992; 52(11):3131–7.

MSDS, Gold, Johnson Matthey Aesar Group, 1985.

Darien, B.J. et al. Scanning Micros. 9, 773 (1995).

Hillyer, J.F. and Albrecht, R.M . Micros. and Microanal.., Bailey, GW, ed. (1998). p.998.

Brown JM, et al. The unique physiology of solid tumors: opportunities (and problems) for cancer therapy. Cancer Res. Apr. 1, 1998; 58(7):1408–16.

Mittleman, A. "Life–threatening toxicity of cancer therapy", Crit. Care Clin. 4, 1–9, 1988.

Moore IM. Central nervous system toxicity of cancer therapy in children. J. Pediatr Oncol Nurs. Oct. 1995;12(4):203–10; discussion 211.

Maher LJ 3rd. Prospects for the therapeutic use of antigene oligonucleotides. Cancer Invest. 1996; 14(1):66–82.

Qasim FJ, et al. Gold and D–penicillamine induce vasculitis and up–regulate mRNA for Il–4 in the Brown Norway rat: support for a role for Th2 cell activity. Clin Exp Immunol. Jun. 1997;108(3):438–45.

Takahashi Y, et al. The utility of chelating agents as antidotes for nephrotoxicity of gold sodium thiomalate in adjuvnat–arthritic rats. Toxicology. Mar. 31, 1995;97(1–3):151–7.

Tomioka R, et al. Gold–induced pulmonary disease: clinical features, outcome, and differentiation from rheumatoid disease. Am J Respir Crit Care Med. Mar. 1997;155(3):1011–20.

* cited by examiner

LOADING METAL PARTICLES INTO CELL MEMBRANE VESICLES AND METAL PARTICULAR USE FOR IMAGING AND THERAPY

CROSS-REFERENCE TO RELATED APPLICATIONS

This application is entitled to the benefit of Provisional Patent Application Ser. No. 60/094,669 filed Jul. 30, 1998.

BACKGROUND

1. Field of Invention

This invention relates to medical imaging and therapy.

2. Discussion of Prior Art

Cancer Therapy

The National Cancer Institute estimates that over 1,200,000 new cases of invasive cancer will be diagnosed this year in the United States. This means that 46.6% of men (1 in 2) and 38.0% of women (1 in 3) will develop invasive cancer during their lifetime.

Although advances in treatment have occurred, unfortunately each year, more than 550,000 Americans die of cancer—more than 1,500 people a day. It is the second leading cause of death after heart disease. The financial costs of cancer are also staggering. The National Cancer Institute estimates overall annual costs for cancer at $107 billion.

Existing Therapies

Treatment of cancer is an area of intense research interest, and an urgent priority for world health. Although much progress has been made, much effort must still be expended to achieve fully satisfactory tumor control using effective and economical methods. Surgery, radiation, and chemotherapy remain the principal modalities of treatment. New chemotherapeutic agents such as paclitaxel (Johnson D H, J. Natl. Cancer Inst. Monogr. 19, 61, 1995) have been proven highly effective against some cancers, including breast, advanced ovarian, Kaposi's and non-small-cell lung cancers. Our rapidly expanding knowledge of tumor biology has enabled the development of important new approaches to therapy. Elucidation of the structure and function of the receptors and proteins expressed during tumor growth have enabled the development of a new generation of highly effective antibodies for immunotherapy; for example, humanized monoclonal antibodies against the Her-2/neu protein p185 overexpressed in more aggressive breast tumors have proven to be effective against advanced breast cancer (Baselga, J. et al. J. Clin. Oncol. 14, 737, 1996). Understanding the genetics of cancer, and the role of oncogenes and gene amplification has enabled researchers to pursue therapies which directly target the genetic abnormalities found in tumor cells, such as antisense therapy (Hung, M. C. et al. Gene,159, 65, 1995) and gene therapy (Yan, D. H. Biochem. Biophys. Res. Commun. 246, 353, 1998). Research into the molecular basis for the effect of tumors on surrounding blood vessels (angiogenesis, Fidler, I. J., et al. Cancer J. Sci. Am., Suppl. 1, 4, S58, 1998) has brought a new class of therapeutics into consideration which intervene in this process, such as anti-angiogenic antibodies (Presta, L. G., et al. Cancer Res. 57, 4593, 1997), peptides and polypeptides such as angiostatin, endostatin, and VEGF (Boehm, T., et al. Nature 390, 404, 1997). However, these approaches alone have not resulted in universal new therapies: for effective application, they require intensive research into those processes in the specific cancer to which the therapy is targeted.

Significant advances have also been made in liposome delivery agents (Dass, C. R. agents such as boron compounds for Boron Neutron Capture Therapy (BNCT, Gahbauer, R. et al. Recent Results Cancer Res. 150, 183, 1998) and radioimmunochelates for radiotherapy (Faivre-Chauvet, A. et al., Nucl. Med. Comm. 17, 781, 1996) has made these approaches more clinically relevant.

The most commonly used therapies are surgery, radiation, and chemotherapy. The deficiencies of each treatment are well known: Surgery cannot be used with inoperable tumors, for example in the brain or when vital organs are entangled, or fails to prevent recurrences when not all of the tumor and metastases are removed. Radiation frequently has a limited benefit: lethal doses to normal tissue must be avoided, therefore making the required tumoricidal dose unachievable; also some tumors are radioresistant: " . . . hypoxia in solid tumors leads to resistance to radiotherapy and to some anticancer drugs" (Brown, J. M. and Giaccia, A. J., Cancer Research, 58, 1408–16, 1998). Chemotherapy suffers from toxicity, limiting the amount of drug that can be administered. "The use of chemotherapeutic agents in the therapy of cancer has led many physicians to increase the dose of these agent in the hopes of increasing efficacy. Increasing dosages caused an increase in the toxicity, which was occasionally life threatening and required aggressive therapeutic measures." (Mittleman, A. "Life-threatening toxicity of cancer therapy", Crit. Care Clin. 4, 1–9, 1998); " . . . chemotherapy and whole brain radiation are associated with acute, subacute, and delayed toxicities", (Moore, I. M., "Central nervous system toxicity of cancer therapy in children", J. Pdiatr. Oncol. Nurs. 12, 203–210, 1995).

Newer, experimental therapies and drugs may seem promising, but these too, have shown shortcomings. They are useful, however, since they have provided relief or remission in some cases. Anti-angiogenic therapy, which attempts to prevent proliferation of blood vessels required to support tumor growth, is an interesting new method, but clinical trials have often been disappointing, and most patients continue to succumb. Radioimmunotherapy has been tried, but the toxicity of radiation delivered to non-tumor tissue has limited its use and success. Gene therapy has likewise thus far not been generally successful clinically; " . . . current strategies for oligonucleotide-directed triple helix formation suffer from important constraints involving requirements for stabilizing binding conditions, restrictions on permitted target sequences, and inefficient nuclear delivery of oligonucleotides. Implementation of oligonucleotide-directed triple helix formation as a viable approach to cancer therapy must therefore await clever solutions to a series of fascinating problems." (Maher, L. J. $3^{rd}$,"Prospects for the therapeutic use of antigene oligonucleotides", Cancer Invest. 14, 66–82, 1996). Antibody therapy has shown to be of some benefit for certain cancers, but many do not respond. Boron neutron capture therapy has been under development for over 20 years and even now does not improve patient survival over conventional therapy. New drugs, such as paclitaxel and others have shown promise, extending life in some individuals, but recurrences and non-responders are common.

Although progress is being made, the cancer death rate has sadly not improved significantly over the years. It is fair to say that with so much effort and expense in cancer research, the development of a substantial new therapy that overcomes the limitations of previous attempts and current technology is not obvious.

Surgery attempts to remove the tumor, which is not completely possible in many cases. Cells that have metastasized and spread are not removed. Also, some tumor cells may be physically left behind and then regrow the tumor. Other tumor cells may be too difficult for the surgeon to selectively remove without risking important other tissues, commonly the case in pancreatic, brain, and liver cancer. An additional type of therapy used in conjunction with surgery is therefore required. Most other cancer therapies are based upon a cytotoxic effect, for example, the use of radiation and drugs. The toxic agent or radiation must be directed to the tumor since these are also toxic to normal tissues. Herein lies the problem. Useful chemotherapeutic drugs have some enhanced targeting or effect on tumor cells, but unfortunately they are still toxic to normal cells as the dose is raised, frequently limiting delivery of enough to eradicate all of the tumor. Similarly, radiation treatments, although regionally directed, still hit normal tissue, limiting the dose. Because some tumors or tumor regions are resistant to radiotherapy, this also limits effectiveness. What is needed in an improved therapy is more selective delivery of the cytotoxic effect to tumor cells.

Complete eradication of the tumor is a formidable task. Solid tumors (carcinomas) have been shown to be microscopically heterogeneous e.g., in expression of tumor markers and growth. Most anticancer drugs or therapeutic agents (including chemicals, nucleic acids, antibodies, radioisotopes, etc.) are based on a preferred affinity for tumor cells. This is then complicated by the heterogeneity of the tumor. Too little of the agent may accumulate on some of the cells, and they will thusly escape therapy. For example, an antibody strategy may be foiled by the various levels of target antigen expressed on different tumor cells. Drugs and radioisotopes may have a limited range that is insufficient or incapable of reaching adjacent but undertargeted cells. Another problem is that carcinomas are separated from the blood by the vasculature walls, so that any drug or agent administered intravenously must pass through the vessel walls to get to the tumor cells. This limitation can be a severe restriction in the brain due to the blood brain barrier. Although tumor vasculature is more "leaky", this is usually in the necrotic regions rather than the more important growing periphery of the tumor. Furthermore, the drug or agent must penetrate and be able to reach to sufficient concentration all cells in the tumor mass.

Boron neutron capture therapy (BNCT) is a novel experimental approach now being tried clinically for treatment of brain tumors. It is based upon delivery of boron-10 to the tumor, then irradiation with neutrons from a reactor which fissions the boron into an alpha and lithium particles. Unfortunately, to date, life expectancy has not been statistically extended by this procedure. Several drawbacks have now become evident: the 30 parts per million of boron-10 required for cytotoxicity may not have been achieved in all tumor cells. Since the range of the destructive alpha and lithium particles is only about 5 microns, adequate concentration in one cell will not be effective for killing a neighboring tumor cell with too little boron because of this short range. Another worry is that tumor to non-tumor ratios of boron-10 achieved are in the order of 3 to 1, and may be less than that marginal value in some regions.

Angiogenesis (formation of new blood vessels) is now of high interest, since blocking new blood supply would inhibit tumor growth. A number of substances that stimulate and inhibit angiogenesis have now been identified (McNamara, D. A. et al. Brit. J. Surg. 85, 1044, 1998). Unfortunately, the use of anti-angiogenic substances for cancer therapy has encountered several difficulties that have limited its clinical value: a) since there are many angiogenic substances, therapy consisting of inhibition of one or a few of these may slow the process, but not eliminate it, since other angiogenic substances which are not blocked continue to function; b) Although angiogenic inhibitors may block proliferation of vessels needed to support internal tumor growth, cells at the growing tumor periphery derive some nutrients from normal vessels and continue to grow (Huang, X., et al. Science 275, 547, 1997); c) A further disadvantage is that antiangiogenic therapy must be administered continuously to keep tumor vessels in check since the tumor cells are not killed.

A thorough review of all existing and experimental therapies is not given here, but each appears to have limitations, and although some progress and relief has been achieved, the overall death rate remains high for this disease (about 46%, deaths per new cases diagnosed).

Any proposed novel therapy that may overcome some of the problems and limitations of current technology will have to be submitted to extensive testing and trials that will take years before complete evaluation of efficacy and limitations are known and clinical use is begun. However, the conception and invention of such a therapy should be registered and acknowledged.

Heart Disease, Stroke, and Atherosclerosis

1996 U.S. statistics show that coronary heart disease (which causes heart attack and angina) is the single leading cause of death in America, amounting to 476,124 deaths in the United States in 1996 (one of every 4.9 deaths). There are about 1,100,000 new and recurrent cases of coronary attack per year in the U.S.; of these, about one-third die, based on data from the National Heart, Lung, and Blood Institute's Atherosclerotic Risk in Communities (ARIC) Study, 1987–94. More than 900,000 Americans die each year from cardiovascular causes, including stroke, hypertension, congestive heart failure, atherosclerosis, and congenital heart defects, according to American Heart Association estimates.

Prophylaxis includes altering risk factors we may modify including: cigarette and tobacco smoke, high blood cholesterol, high blood pressure, physical inactivity, obesity and overweight, and diabetes mellitus. The decline in death rates from cardiovascular disease in the United States is due largely to the public's adopting a more healthful lifestyle. Evidence shows that atherosclerotic plaques can regress in people with the disease. Besides better diet, exercise, and not smoking, there are useful pharmaceuticals that reduce blood pressure, cholesterol, and control diabetes. Although having an impact, all these measures are woefully inadequate when the high death rate is considered.

Treatment of myocardial infarction or stroke may be by drugs that can reduce the clot enzymatically, such as with tissue plasminogen activator (TPA), streptokinase, or agents that inhibit platelet action, such as with monoclonal antibodies or aspirin. Mechanical procedures include coronary artery bypass graft surgery (CABG), laser angioplasty, percutaneous transluminal coronary angioplasty (PTCA or balloon angioplasty). About one-third of patients undergoing the PTCA procedure have renewed narrowing (restenosis) of the widened segment within about six months of the procedure.

Although all of these therapies significantly save many lives, they fall far short of what is needed, as evidenced by the continued high death rate.

Atherosclerosis involves deposits of fatty substances, cholesterol, cellular waste products, calcium and fibrin in the inner lining of an artery, forming plaque. This may partially or totally block blood flow through an artery. Additionally, there may be hemorrhaging into the plaque, or formation of a blood clot (thrombus) on the plaque's surface. If either of these occurs and blocks the entire artery, a heart attack or stroke may result. Atherosclerosis is a slow, progressive disease. One theory is that the endothelium of the artery becomes damaged due to elevated blood levels of cholesterol and triglyceride, high blood pressure, cigarette smoke, or other factors. This damage stimulates deposition over time of fats, cholesterol, fibrin, platelets, cellular debris, and calcium. The deposits can reduce or stop blood flow, or may break away, stimulating thrombosis. One theory suggests that excess lipoproteins in the blood are trapped within the artery wall and become oxidized. These modified lipoproteins are rapidly taken up by smooth muscle cells, which leads to the formation of foam cells and subsequent deposition of connective tissue cells and elements. Platelets also play a role in atherosclerosis. In addition to being involved with clot formation, they also produce prostaglandins, which may damage arteries. They can also release platelet derived growth factor (PDGF) which stimulates the growth of smooth muscle cells in the artery wall, one of the earliest events in the atherosclerosis process.

Although much is known about the cause and progression of vascular disease, the available pharmaceuticals along with other preventative measures (such as diet, exercise, and not smoking) fall far short of effectively preventing fatal complications for vast numbers of persons.

Kidney Disease

According to the U.S. National Institute of Diabetes, Digestive, and Kidney Disease (NIDDK) of the National Institutes of Health, the End Stage Renal Disease (ESRD) population in the US is composed of more than 200,000 patients who undergo dialysis and 70,000 patients with functioning kidney transplants. The ESRD population is growing at a rate between 7–9 percent per year. By 2010, there will be more than 350,000 such patients. Diabetes is the leading cause of ESRD (35% of all newly diagnosed cases). Among black Americans, however, hypertension is the most common cause (40%). Total life expectancy for adults with ESRD is still less than a decade, a figure similar to that for cancer. US mortality rates have now exceeded 25% per year. Kidney disease is the fifth most common cause of death in the U.S. One out of every 20 Americans, more than 20 million individuals, suffers from diseases of the kidney and urinary tract.

The two most common causes of kidney disease are diabetes and high blood pressure. In diabetes, high blood sugar acts like a poison, damaging the kidneys' filters (nephrons). High blood pressure can damage the small blood vessels of the kidneys. In glomerulonephritis, nephrons become inflamed and scarred and slowly lose their ability to remove wastes and excess water from the blood to make urine. Diabetic nephropathy, IgA nephropathy, and lupus nephritis are some types of glomerulonephritis. Symptoms and signs of this disease are fatigue, high blood pressure, swelling, especially noticeable in the face, hands, feet, and ankles, and blood and protein in the urine. Unfortunately, the kidneys can be severely damaged before symptoms appear.

Kidney disease cannot be cured. Treatments focus on slowing the progression of the disease and preventing complications. Angiotensin converting enzyme (ACE) inhibitors have a protective effect on the kidneys in diabetic patients and lower high blood pressure. Reducing dietary protein, sodium, potassium and cholesterol may also be beneficial. After about 10 years, the disease may progress to kidney failure, when the patient will need dialysis or a kidney transplant.

It is clear that there is a need for improved treatment of this disease.

Alzheimer's Disease

Alzheimer's disease (AD) is a progressive, neurodegenerative disease characterized by memory loss, language deterioration, impaired visuospatial skills, poor judgment, indifferent attitude, but preserved motor function. AD usually begins after age 60, however its onset may occur as early as age 40, appearing first as memory decline and, over several years, destroying cognition, personality, and ability to function. Approximately 4 million Americans have AD. One in 10 persons over 65 and nearly half of those over 85 have AD, and increasingly it is found in people in their 40s and 50s. AD costs society (U.S.) approximately $100 billion a year. Neither Medicare nor private health insurance covers the long term type of care most patients need. According to the National Institutes of Health, "There is no cure for AD and no way to slow the progression of the disease."

Morphologically, AD is characterized by neurofibrillary tangles which are intracellular clumps or knots of neurofibrils composed of paired helical filaments of tau protein within individual diseased neurons, and senile plaques which are microscopic lesions made up of fragmented axon terminals and dendrites enveloping a core of beta-amyloid protein. Why these proteins accumulate extensively in the brain is not known.

Obesity

The U.S. Surgeon General, in a 1988 report on nutrition and health, estimated that 25% of adult Americans are overweight. Obesity is not just a cosmetic problem, but a health hazard. People who are overweight have a greater chance of developing high blood pressure, high blood cholesterol, type 2 diabetes, heart disease, stroke, and certain cancers.

As a result of genetics, diet, and overeating, adipocytes (fat cells) store excess lipids and increase in size, and may be stimulated to divide. Weight reduction plans include altering diet, drugs, and physical removal of adipose tissue, such as with liposuction. Unfortunately, although adipocytes may be forced to burn fat and reduce in size with dieting or drugs, their increased number remains, and when a diet lapses, they may more readily expand and the obesity quickly returns. Diets are also difficult to maintain. Additionally, drugs pose risks and side effects. Liposuction is expensive, generally a non-reimbursable expense (by health care companies), carries some risk, and is only partially effective.

More effective treatments of obesity are needed.

Tuberculosis

Tuberculosis (TB) is a chronic bacterial infection, and causes more deaths worldwide than any other infectious disease. TB is spread through the air and usually infects the lungs, although other organs are sometimes involved. Some 1.7 billion people—one-third of the world's population—are infected with the predominant TB organism, *Mycobacterium tuberculosis*. Most people infected with *M. tuberculosis* never develop active TB. However, in people with weakened immune systems, especially those infected with the human immunodeficiency virus (HIV), TB organisms may overcome the body's defenses, multiply, and cause active disease. Each year, 8 million people worldwide develop active TB and 3 million die.

In the United States, TB has re-emerged as a serious public health problem. In 1993, a total of 25,287 active TB cases were reported, an increase of 14 percent since 1985. In addition to those with active TB, however, an estimated 15 million people in the United States have latent TB infections and may develop active TB at some time in their lives.

Drug resistance is a concern: The death rate for untreated TB patients is between 40 and 60 percent, but with appropriate antibiotics, drug-susceptible cases can be cured more than 90 percent of the time. However, in recent years, drug-resistant cases of TB have increased dramatically. Particularly alarming is the increase in the number of people with multi-drug-resistant TB (MDR-TB), caused by *M. tuberculosis* strains resistant to two or more drugs. Even with treatment, the death rate for MDR-TB patients is 40 to 60 percent, the same as for TB patients who receive no treatment. For people coinfected with HIV and MDR-TB, the death rate may be as high as 80 percent. The time from diagnosis to death for some patients with MDR-TB and HIV may be only months as they are sometimes left with no treatment options. Of all culture-positive TB cases in New York State in 1995, at least 13 percent were resistant to one or more antibiotic drugs.

TB is caused by exposure to airborne droplets contaminated with *M. tuberculosis*, a rod-shaped bacterium. The waxy cell wall appears to allow *M. tuberculosis* to survive in its preferred environment: inside macrophages, which ordinarily degrade pathogens with enzymes. The coat of *M. tuberculosis* also renders it impermeable to many common drugs. The site of initial infection is usually the alveoli (sacs at the ends of the small air passages in the lungs known as bronchioles). In the alveoli, macrophages ingest the inhaled *M. tuberculosis* bacilli. The body's immune defenses kill many bacilli, but immune cells and local tissue die as well, forming granulomas where the bacilli survive. As more lung tissue is destroyed and the granulomas expand, cavities in the lungs develop, allowing large numbers of bacilli to spread when patients cough. As the disease progresses, the granulomas liquefy, creating a rich medium in which the bacilli multiply rapidly and spread, creating further lesions and the characteristic chest pain, cough, and, when a blood vessel is eroded, bloody sputum.

Although antibiotics are the mainstay of therapy of TB, increasing drug resistance, and the continued high death rate, mandate that new and effective therapies be developed.

Malaria

Malaria is one of the most serious health problems facing humanity. Approximately 300 million of the world's population are infected by the disease and between 1 and 1.5 million people die from it every year. The situation has become even more complex over the last few years with the increase in resistance to the drugs normally used to combat the parasite (a protozoan, genus Plasmodium) that causes the disease. New, effective therapies are needed.

Other Diseases and Conditions

There are many other diseases and conditions for which there are no known cures and for which the existing treatments are inadequate, not effectively reducing pain, suffering, or stopping the progression to further complications and death.

Medical Imaging

Imaging is an important medical diagnostic and monitoring tool. A number of methods have been created, including x-rays, fluoroscopy, angiography, mammography, computer aided tomography (CAT), positron emission tomography (PET), single photon emission computerized tomography (SPECT), magnetic resonance imaging (MRI), and ultrasound imaging. Some methods may be used either with or without contrasting agents. For example, barium is used for bowel imaging, and Gd-DTPA with MRI for vascular imaging. Although extremely useful, each approach has limitations: some are invasive, carrying some risk to patients, such as the exposure to radiation with x-ray imaging and radioisotopes with SPECT. Others involve surgical risks, such as threading catheters to the heart or head for angiography. Although MRI is considered non-invasive, it has limited resolution, so small lesions cannot be detected. This limitation of resolution of MRI for imaging is well-acknowledged: "Magnetic resonance angiography of the peripheral arteries is limited by spatial resolution and signal loss distal to the stenosis." ( Calabrese, L. C., Wholey, M. H., Arterial imaging, Curr. Opin. Cardiol. 1992 October;7(5):843–50). CAT scans are also recognized to have limitations: "The role of computed tomography in limiting the number of aortograms performed in evaluating aortic laceration remains controversial"(Calabrese, L. C., Wholey, M. H., Arterial imaging, Curr Opin Cardiol 1992 October;7(5):843–50). In fact, all modes have resolution limitations. This becomes crucially important since, for example, early detection of cancer (when tumors are smaller) is correlated with better prognosis. A further limitation of these technologies is that frequently the sought out tissue, whether it is tumor, plaque, or other abnormality, is not highlighted significantly above normal tissue, and escapes detection. The two major technical limitations are therefore resolution and specificity. Two other important limitations are risk and cost. A method that provides a way to overcome some of these restrictions could have a significant impact on the management of relevant diseases and conditions.

Metal Particles

Although colloidal particles and metal clusters have been described, they have not been adapted or applied in the way herein disclosed for medical therapy or imaging. Red-colored gold colloids have been reported as early as the $17^{th}$ century, and their medicinal value based on the belief that blood was the life-essence, and the active principle of blood was redness. Aurum potable of alchemists, called cinnabar-gold, was supposedly endowed with miraculous medicinal virtues, capable of prolonging life, curing all manner of diseases, and rejuvenation. By the $18^{th}$ century, however, it became apparent that the gold tinctures were only finely divided gold in an oily fluid and devoid of any medicinal and therapeutic value (Handley, D. A. (1989), in Hayat, M. A. (Ed.), Colloidal Gold: Principles, Methods, and Applications. Vol. 1, pp. 1–32, Academic Press, San Diego, Calif.). More recently, the closest use has been of various gold formulations for the treatment of rheumatoid arthritis (RA). Typically, single gold atom compounds are used, but these can elicit an allergic reaction ("D-penicillamine and gold salts which are used as immune-modulating agents in the treatment of rheumatoid arthritis are known to be capable of causing autoimmune manifestations." Qasim, F. J, Thiru, S., Gillespie, K., *Clin Exp Immunol* 1997 June; 108(3):438–45). Treatment of with RA with aurothiomalate can also be accompanied by kidney damage (Takahashi, Y., et al., *Toxicology* Mar. 31, 1995;97(1–3):151–7). Other complications also have been reported: "Gold-induced pulmonary disease most often followed improvement in rheumatoid arthritis, presumably induced by gold therapy. . . . Side effects other than pulmonary toxicity were common, and included skin rash (38%), peripheral eosinophilia (38%), liver dysfunction (15%), and proteinuria (22%). Gold-induced lung disease . . . usually improves with cessation of therapy or treatment with corticosteriods." (Tomioka, R., King. T. E. Jr, *Am. J Respir. Crit. Care Med.* 1997 March;155(3):1011–20).

SUMMARY

The present invention describes a method to image or damage cells by delivery of metal particles to cells, then applying external energy that interacts with the metal particles. It also describes a method to load metal into cells or membrane vesicles by placing metal seed particles into the cells or vesicles, then chemically depositing additional metal on the metal seed particles.

DETAILED DESCRIPTION

In its simplest form, the essence of the invention is the use of metal particles for enhanced therapy and imaging. Means have been devised to effect these novel uses and indicate its wider application. The metal particles can passively or actively be delivered to the site of interest. For example, metal particles can fill a compartment, such as vasculature, the bladder, or by injection to a region, or be additionally directed to specific sites by the coating on the metal particle with such directing substances such as antibodies, drugs, peptides, proteins, lipids, carbohydrates, nucleic acids, or other materials. The metal particle can be organometallic compounds, clusters, or colloidal. Enhanced therapy and imaging is then achieved by the interaction of the particles with sources of energy or radiation. For example, x-rays may be used, and interactions with the metal particles useful for increased energy deposition in the vicinity of the particles. This increased localized dose may be used to kill tumor cells, for example. This is hereby called "Metal Enhanced Radiation Therapy", or "MERT". Metal-Enhanced Radiation Therapy (MERT) is a new approach to killing cancer cells in a highly specific manner, because it uses a highly lethal phenomenon—the generation of ionizing radiation by metals under x- and gamma-ray irradiation. The increased absorption and scattering would also effect contrast enhancement for improved imaging. In a similar way, other forms of energy could be used, including gamma rays, microwaves, diathermy sources, alternating current, radio frequencies, ultrasound, proton beams, beams of other particles, laser light, and other forms of radiation. Some sources may be tuned or focused to enhance the interaction effects with the metal particles, such as using particular wavelength x-rays at an absorption edge of the metal. A further part of this invention is the loading of cells, cell membrane vesicles, and synthetic vesicles with metal particles. Metal "seeds" are introduced into the cell or vesicle container, and these seeds are used to nucleate chemical deposition of additional metal, thus more completely filling the container. These encapsulated particles may be either passive, or made with derivatized outer surfaces with directing moieties that would target the metal-laden cells or vesicles to particular sites. The targeting moieties may include antibodies, drugs, peptides, proteins, lipids, carbohydrates, nucleic acids, or other materials. The loading of such cells or vesicles has the advantage of potentially delivering higher concentrations of and more total metal to the site of interest, thus enhancing the therapeutic or imaging effect.

Metals have properties that make them useful for sensing, imaging and therapy. For example, gamma and x-rays are more highly absorbed, scattered, and productive of secondary emissions (particularly upon excitation at certain wavelengths), than from lower atomic number elements such as those comprising tissues. This makes metals ideal for detection and imaging and to enhance the effects of gamma and x-rays on the surrounding tissues. It is here proposed that that delivery of metal particles to tumors would therefore enhance the effectiveness of standard radio-immunotherapy.

Metals also interact with microwaves differently than water or tissues, hence the avoidance of metal items placed in a microwave oven. Metal particles, however, placed in contact with tissue might under controlled conditions be used to focus energy and provide local heating which could be of therapeutic value. Metals also have a different dielectric constant than tissues or other materials. Metal particles in a matrix of tissue or other materials under the influence of an alternating current would demonstrate different induced dipole motion. Diathermy, or the production of heat in body tissues by electric currents, for therapeutic purposes, may be enhanced by the presence metal particles.

Metal particles in contact with soft tissue or material may also show useful behavior when exposed to ultrasound where the high speed agitation of the soft tissue with the hard particles may cause local trauma or cell disruption that would otherwise not occur without the metal particles.

Metal particles might therefore in general be used to effect disruption in materials or necrosis in tissues in the vicinity of the metal particles by a variety of excitations from radiation, sound, electrical or other energy sources. Because of the different interaction of radiation on metals versus other materials, metal particles may be ideal for detection or imaging.

Delivery of metal particles to tumors, tissues, or plaques might be accomplished by passive distribution in the vasculature compartment, thus preferentially contacting endothelial cells, of which dividing cells, such as found in tumors are more radiosensitive. Active delivery of metal particles might be effected by conjugation with directing moieties such as antibodies, peptides, nucleic acids, carbohydrates, lectins, lipids, or other materials that target receptors, antigens, proteins, or act to enhance endocytosis of the particles. Other useful targeting moieties are the YIGSR peptide, a cell adhesive ligand involved in metastasis and angiogenesis, and Sialyl Lewis oligosaccharide, a cell adhesive ligand for E-, P-, and L-selectins involved in inflammation related tissue injury.

A number of drug delivery systems have been proposed, using radioisotopes, cytotoxic agents, liposomes, antibodies and other schemes. Two common limitations of many of these schemes have restricted their usefulness: 1) Toxicity to critical non-tumor tissues being reached before sufficient dose can be achieved at the tumor, and 2) Inadequate delivery of cytotoxic agent to the tumor due to short blood half life, uptake by the reticuloendothelial system (RES), heterogeneous delivery to all tumor cells, finite tumor antigen sites per cell available, or other factors. This leads to incomplete effectiveness of therapy to at least some tumor cells and subsequent recurrence.

Metal particles may overcome some or all of these difficulties by providing multiple metal atoms per antibody or directing moiety attached, thus amplifying the amount delivered compared to one-drug-one-antibody approaches. Metal particles combined with liposomes or other delivery vehicles may also enhance the amount delivered. Metal particles may be colloidal particles or organometallic cluster compounds, such as undecagold, Nanogold, tetrairidium clusters, or the like.

Metal-loaded Cells and Vesicles

In some cases, the amount of metal localized to the target cells may be insufficient. Delivery of larger quantities of the cytotoxic agent to tumors has been addressed by liposome incorporation or encapsulation. However, this approach suffers from a number of limitations. First, even "stealth" liposomes only increase the blood half-life from minutes to generally hours. Secondly, standard encapsulation works by passive inclusion of the agent in the solution in which the liposomes are formed. A 0.1 molar solution of gold atoms would lead to 6.3×10E7 molecules in a 1 micron diameter vesicle, whereas a vesicle of the same size filled with solid gold would contain 5.2×10E10 atoms, or a factor of ~825 times higher gold. Such a highly filled vesicle would greatly improve metal delivery. Another problem with standard liposome technology is that the liposomes may be immunogenic.

All of the above deficiencies may be overcome by the present invention. Normal autologous cells are used as delivery vessels. Since erythrocytes have a blood life of ~120 days, their use may avoid rapid clearance in the liver and spleen by the reticuloendothelial system (RES), as is common for liposomes. Autologous cells will not be immunogenic. Loading of the cell membranes includes an active chemical step, which can fill the enclosed volume with metal, thus enabling extremely high loading. The metal particle loaded cells may be used as is, or directing moieties may be attached to their surface such as antibodies, peptides, or other substances.

The metal containing cells (or smaller cell membrane vesicles), are here coined as "METALLOCYTES", or if they contain gold, they are termed "AUROCYTES". Full cell sized metallocytes may be too large to leave the vasculature to reach tumor cells. However, enhanced radiative effects on the vasculature endothelium due to metal in the vessel would be expected to damage growing endothelium, as is found in tumors, to a greater extent than normal, non-dividing endothelium, thus enhancing the radiation treatment by compromising blood supply selectively to tumors.

A number of endothelial markers have been and are being described for specific tumor neovasculature and antibodies, peptides, or other binding moieties to such markers may be bound to the metallocytes to enhance tumor vasculature targeting and subsequent radiative or energy interaction disruption.

Metallocytes may be made smaller for some purposes, such as for better passage through capillaries and small blood vessels, or better accumulation in breached blood brain barrier accompanying brain tumors, or leaky vasculature found in tumors, or optimizing size for endocytosis, ink jet delivery, or other specialized applications. Small metallocytes may be made from fragments of whole cell membranes, so their normal autologous outer surface is still presented. This aids in evading normal body responses that clear foreign matter. Small metallocytes may also be made using synthetic liposome vesicles, if desired.

Specific targeting of metal locytes may be accomplished by attaching to the outer surface antibodies, antibody fragments, peptides, nucleic acids, lectins, charged moieties, lipids, or other molecules that bind the desired target.

The surface of the metallocytes may also be directly modified to yield desired surface properties, either by enzyme action, such as sialidase, chemical reaction, such as acetylation, or insertion of lipids.

Although cells as carriers have previously been described, they suffered from low loading and did not address metal particle delivery. This work has solved the previous shortcomings by a novel process that first opens the membrane either by hypotonic lysis or detergents, then passively loads small nucleating metal particles within the cells, the size of the membrane hole or holes is reduced (by higher salt, temperature, or lower detergent, or other means) to retain the nucleating particles so the cells can be washed free of extracellular particles, and finally additional metal is catalytically deposited on the nucleating particles to grow them to the desired size and loading. Because the growth solution is composed of metal ions as the source of metal, they can easily access the cell vesicle interiors. Growth of external particles is avoided since there are no nucleating particles to start deposition in that compartment. Preferably, the nucleating particles are grown to a size which occupies more than 10 percent ofl the internal volume of the cell vesicle. Growth may be continued even until the cell vesicles are almost entirely filled by the deposited metal. Smaller sized cell membrane vesicles containing metal particles are formed similarly, but the full cells are homogenized before development with metal ions, by passage through a small bore syringe, sonication, or other means. The nucleating metal particles may also be actively targeted to the interior wall of the cell membranes, using for example, an antibody attached to the particle, for example anti-actin, anti-ankyrin, anti-spectrin, or other directing moiety.

Since synthetic liposomes have been made that mimic cell membranes to some degree, the methods described can also be extended to synthetic liposomes by those skilled in the art, to encapsulate metal particles by the active metal deposition. Catalytic metal deposition goes by various names such as autometallography, electroless plating, metal enhancement, or metal development, and requires a catalytic surface for deposition (here small gold metal particles are used, but other materials are also suitable), and a reducing agent, such as hydroquinone. Other agents are typically added to control the process, to make the development more uniform, reduce background, control the speed, or other parameters. Many different metals can be deposited including gold, silver, nickel, copper, cobalt, alloys, platinum, and palladium.

Theoretical Basis of Metal-radiation Interactions

As radiation penetrates matter, it is attenuated, resulting in the transfer of energy to secondary nonpenetrating radiation which deposits energy locally. By increasing the interaction within a treatment volume, the energy deposited to that volume will be increased, enhancing the potential for therapeutic benefit. This is precisely the goal of loading metal within the tumor volume.

The equation which describes the fraction attenuated is:

$$[1-(I/I_o)]=1-\exp(-\mu_m \rho x) \qquad \text{(equation \#1)}$$

where I is the transmitted intensity, $I_o$ is the initial intensity, $\mu_m$ is the mass attenuation coefficient, $\rho$ is the density of the material and x is the thickness of material traversed.

The total attenuation is primarily the result of three basic processes at energies routinely employed in modern external photon beam radiation therapy: photoelectric interaction, Compton effect and pair production. For the photoelectric effect, the mass attenuation coefficient component depends on incident photon energy (E) and target atomic number (Z) as $[Z/E]^3$. The relative probability of interaction per unit mass via photoelectric effect for gold (Z=79) compared to soft tissue (Zeff of water=7.4) is 1217. The nonpenetrating secondary radiation emitted are photoelectrons (having mm ranges) and Auger electrons (having micrometer ranges or a few cells). For the Compton effect, the mass attenuation coefficient component varies as approximately [Z/A], where A is the mass number. As a result, the Compton component of mass attenuation coefficient is only slightly different between air and gold, but because of greater density (17 g/cc for gold compared to 1 g/cc for tissue), gold still provides superior attenuation. The nonpenetrating secondary radiation associated with the Compton effect are recoil electrons. Pair production varies as $Z^2$ [log E]. Therefore, the relative pair production component of the mass attenuation coefficient of gold compared to water is approximately 114. The nonpenetrating radiation associated with this process are electrons and positrons.

As a result of the above considerations, gold will provide better absorption of photons than tissue. Enhanced attenuation maybe three orders of magnitude at energies where photoelectric effect dominates (<1 MeV), two orders of magnitude where pair production dominates (>15 MeV) and more than an order of magnitude where Compton dominates. Likewise, the future application of the technology of gold (or other suitable metal) loading will require photon energy optimization to the clinical need. For example, superficial applications would benefit form the use of low energy (k-edge) photons while deep-seated applications may require high energy photons.

From a dosimetric point of view, the fraction change in local dose which will result from the presence of gold can be estimated from the following:

$$D \propto \{[(\mu_{en}/\rho)_{Au} \times f_{Au}] + [(\mu_{en}/\rho)_{tiss} \times (1-f_{Au})]\}/[(\mu_{en}/\rho)_{tiss}] \quad \text{(equation \#2)}$$

where $(\mu_{en}/\rho)$ is the mass energy absorption coefficient of gold (Au) or tissue (tiss) and f is the fraction by mass of gold (Au). This will be the case if gold is assumed to have negligible electron stopping power. This assumption is true given that the fraction of gold by weight is small. This assumption also simplifies equation #2:

$$D \propto 1 + f_{Au}\{[(\mu_{en}/\rho)_{Au}]/[(\mu_{en}/\rho)_{tiss}]\} \quad \text{(equation \#3)}$$

The dose improvement then will be directly dependent on the fraction of gold loaded and the ratio of the mass energy absorption coefficients of gold to tissue. This ratio depends upon the interaction that dominates. At 0.05 MeV (photoelectric dominated) the ratio is approximately 150. At 20 MeV this ratio is approximately 3.

From the above, the presence of gold will result in enhanced absorption within the treatment volume. For gold present in a relative concentration of $2 \times 10^{-5}$ with in the treatment volume, the enhancement in macroscopic dose is only 0.3% even in the photoelectric domain. From this point of view, there is only a minor effect on macroscopic dose and it is certainly of questionable clinical benefit. On the other hand, metal concentration within tumor cells has been measured at between $5 \times 10^{-3}$ and $4 \times 10^{-1}$. The corresponding dose improvement here is between 75% and 6000% in the photoelectric dominated region and up to nearly 120% improvement at high energy. This clearly has important clinical implications. The external photon beam is little modulated by the presence of gold, so conventional treatment planning methods may be employed, yet the presence of gold can significantly enhance to dose to tumor.

The references for the relative gold concentrations listed above ($5 \times 10^{-3}$ and $4 \times 10^{-1}$) are: a) Personal communication from E. de Harven, after he measured the average gold loading per tumor cell described in De Harven, E. et al. Cancer Res. 52, 3131 (1992), and b) amount of gold calculated per cell based on the reference Haigler, H. T., McKanna, J. A, Cohen, S. J.Cell Biol. 81, 382 (1979), if it is assumed that the number of colloidal gold-EGF particles per cell is equal to the number of ferritin-EGF molecules per cell. (Ferritin is 12.5 nm in diameter, about the same size as colloidal gold.). The first reference was a direct measurement, and the latter therefore indirect.

The above discussion does not cover theoretical details of all metal-radiation interactions but is given only as an example to indicate the theoretical basis of enhancement of radiation therapy when gold is used. Similar or more detailed calculations may be done by those skilled in the art for other forms of radiation and metals.

Objects and Advantages

It is the object of the present invention to improve imaging and therapies by use of metal particles and energy delivered to them.

Cancer Therapy

The current invention overcomes many of the impediments of other methods. It is viewed to be useful in conjunction with other modalities to effect improved responses in patients.

Advantages Over Chemotherapy

A common problem with most existing therapies is that the cytotoxicity is not well enough confined to only tumor cells. For example, chemotherapy is generally limited by the dose that can be administered by the side effects, or toxicity to other organs. The present invention overcomes this difficulty by being a two step procedure: 1) The metal particles are directed to the tumor cells passively or by the targeting moiety attached to them, and 2) the radiation applied is restricted to the tumor region. This means that for example, a treatment of a tumor in the brain should not be toxic to other vital organs, like the bone marrow or kidneys, since the radiation would not be applied to them. This overcomes the major significant drawback of chemotherapy, radioimmunotherapy, cytotoxin-immunotherapy, and other therapies relying on single step tumor localization. Many metal particles, such as gold, have low toxicity and are not expected to seriously affect regions where radiation is not applied.

Material Safety Data Sheets (MSDS) show that gold and gold powder have low toxicity, or that it is not established: "there is no toxicological data available for gold, but toxicity is thought to be very low. Contact of gold with the skin may cause allergic reaction." (MSDS, Gold, Johnson Matthey Aesar Group, 1985). However, several more recent relevant studies have appeared: one where 0.4 g of 16 nm colloidal gold coated with albumen was injected I.V. into 10 week old pigs without any toxic effects (Darien, B. J. et al. Scanning Micros. 9, 773 (1995)). Similar high levels of gold were I.V. injected into BALB/c mice without any toxicity noted (Hillyer, J. F. and Albrecht, R. M . Micros. and Microanal., Bailey, G W, ed. (1998) p.998).

Due to the localized region of treatment (where the irradiation is applied, thus avoiding damage to the rest of the body) and the low toxicity of gold (or other metal) particles, higher levels of reagents can therefore be used than with other chemo agents.

Use of metal particles also simplifies rational design to achieve specific tumor targeting. A better drug does not have to be discovered, but only optimization of the metal particle and conjugation to a tumor-specific targeting molecule (e.g., antibody or peptide).

Advantages Over Radiotherapy

Radiation therapy may lack the elegance of rational molecular approaches, but it remains one of the most highly used treatment modalities for cancer. The addition of MERT should make this tried and true method even more effective. The expected benefits of MERT over standard practices include:

1. Enhancement of effect of radiation.
2. Lower dose to patient.
3. Better responses for patients normally not completely responding with the maximum tolerated dose allowed.
4. Selective deposition of energy to tumor-only regions; more normal tissue is spared.
5. MERT uses standard x- and γ-radiation sources.

Advantages Over Boron Neutron Capture Therapy (BNCT)

1. A nuclear reactor is not required.
2. $^{10}$B fission only has a range of ~5 microns, gold in MERT may affect 50 microns or more, thus making it more effective, killing more cells in the tumor. This is especially crucial since tumors are inhomogeneous, and boron uptake or metal uptake may vary cell to cell. In the BNCT case, low uptake even in one cell will allow the tumor to survive and regrow. With MERT, surrounding cells, even those with lower uptake will be killed, and more effective eradication of the tumor achieved.
3. $^{10}$B concentration must be 30 ppm per cell; for antibody targeting this requires ~1,000 boron atoms/antibody which has been difficult to achieve (Gahbauer, R. et al. Recent Results Cancer Res. 150, 183 (1998)). With gold chemistry, it is possible to attach 100,000 (or more) gold atoms to an antibody and maintain its activity. A simple demonstration of this is the home pregnancy test which uses antibodies attached to ~30 nm gold particles (~1,600,000 gold atoms per particle, having a pink color) for detection.

Advantages Over Angiogenic Therapies

MERT should overcome some of the major limitations of the promising angiogenic inhibitor approach, which seeks to stop the proliferation of blood vessels needed to support tumor growth:

1. Although angiogenic inhibitors may cut off the increased supply of blood required by the tumor, cells at the growing tumor periphery derive some nutrients from normal vessels and continue to grow (Huang, X., et al. Science 275, 547 (1997)). Using the metal/irradiation approach, these peripheral cells may be killed.
2. There are many angiogenic substances (McNamara, D. A. et al. Brit. J. Surg. 85, 1044 (1998)), and therapy consisting of a few of these may slow the process, but not eliminate it, since other angiogenic substances which are not blocked continue to function. In the MERT approach, irradiation actively destroys endothelial and tumor cells.
3, Antiangiogenic therapy must be administered continuously to keep tumor vessels in check; MERT does not, since tumor cells are killed rather than just held in check.

Other Advantages

1. Cell killing range can be controlled by the energy of the primary beam: The extent of damage from the metal particles can actually be controlled externally by adjusting the x-ray energy, providing better control on the number of cells killed by the metal particles.
2. Because metal particles (e.g., gold, iridium, silver, platinum) can be conjugated to many types of biological targeting agents, selective delivery to many of the expressed proteins involved in tumor growth and metastasis can be achieved. Since most cancer patients die from metastases, a more effective modality for metastatic growths is vitally important.
3. The method should be applicable to a wide variety of cancers. The main requirement is that metal be preferentially localized to the tumor. Many targeting methods are now known, including antibodies, peptides, and possibly physical methods such as application of slowly diffusing gold particles applied directly to the tumor or after tumor resection, or injection of gold into an artery supplying the tumor.
4. Application of metal particles to enclosed compartments, such as the bladder (for bladder carcinoma), or via local injection or application, may also be used to enhance delivery by raising the concentration over what would be possible by intravenous administration. Metal particles, delivered passively or actively, by, for example, using an antibody or peptide, may in some cases provide enough metal to be therapeutically sufficient.
5. An additional advantage of the invention, when combining metal particle delivery with x-ray or gamma-ray therapy, is that conventional radiation sources, commonly available in most hospitals can be used. Similar procedures to those currently widely practiced could be used, but radiation applied after administration of the metal particle reagent. This would then greatly enhance the therapeutic value of the radiation. This is in contrast to other experimental therapies that have restrictions, such as Boron Neutron Capture Therapy, which requires a nuclear reactor, or radioimmunotherapy which requires handling and disposal of hazardous radioactive materials.

Metal Particle Delivery Methods

An important part of cancer therapy is achieving a higher cytotoxic level in the tumor compared to normal tissue. However, since dividing normal and tumor cells are more radiosensitive, even a homogeneous distribution of a metal, for example, in the vasculature, may be used to effect a lethal dose to proliferating endothelial cells, thus cutting off the new blood vessel growth needed to support tumor growth. Delivery in this case may be classified as passive. Active delivery may substantially enhance the tumor to non-tumor ratio of metal, and hence lead to improved therapeutic results. Many localization methods are known, including use of antibodies, drugs, peptides, proteins, lipids, lectins, carbohydrates, nucleic acids, and other materials. These materials can be adsorbed or covalently attached to metal particles (colloids and clusters). An additional method of targeting is to make the metal particle surface with a charge that is positive, negative, or neutral, or to endow it with hydrophobic or hydrophilic properties. Such particles then acquire binding affinities for particular tissues.

A special mode of targeting that is peculiar and relevant is that of receptor mediated endocytosis (RME). Cell surface receptors, such as the transferrin receptor or epidermal growth factor receptor (EGFr), normally specifically bind the ligands transferrin or epidermal growth factor (EGF), respectively, then internalize them into the cell where the ligand (e.g., transferrin) is released, and the receptor molecule is recycled to the outer cell membrane, ready to transport another ligand. It has been known that molecules attached to ligands can also be endocytosed, for example ferritin or gold colloid attached to EGF. Also some antibodies, antibodies to receptors, and conjugates of these antibodies can be internalized. Investigators have used this route for delivery of radioisotopes or cytotoxins to tumor cells, but with limited success. One significant problem is that the delivered cytotoxic material once in the cell is subject to enzyme attack, especially in the lysosomes, can be broken down, and frequently diffuses out of the cell in a short period. This is common with radioisotopes. The desired concentration and uptake required for therapy is therefore not attained. A significant advantage of the present invention is that metal particles do get endocytosed when attached to the proper ligand, but are so stable that they just accumulate in the cell, usually in vesicles, and do not diffuse out of or are otherwise ejected from the cell. The present invention identifies and uses this unusual property to accumulate the required amounts of metal in cells for effective therapy.

In tumors, certain receptors are frequently overexpressed, for example, EGFr and transferrin receptor, and this then provides a specific target for metal particles that are properly coated, to selectively accumulate in tumor tissue. Since the metal particles do not escape the cells (at least on an approximate week or month time span), the metal particle conjugated to a receptor specific substance, for example, anti-EGFr antibody,-can be administered over a rather long period, for example a few days or a week, then discontinued to clear the blood, then the radiation applied. This method is not known in the art, but can lead to significant therapeutic advantage.

Although some receptor-ligand systems are well understood, cells are also known to preferentially internalize various other substances, by perhaps different or less well understood means, and some are more active in this regard, such as macrophages. Therefore, metal particles may in general be more selectively delivered to specific cell populations by adjusting the properties of the metal particles, which includes altering the molecules attached to them.

Heart Disease, Stroke, and Atherosclerosis

The present invention pertains to heart disease, stroke and atherosclerosis, since these involve the ill effects of unwanted tissue and plaque accumulation which can be altered by the metal-radiation technique.

In atherosclerosis, there are two types of plaque, one that is loose and one that is fibrous. The loose one is associated with high risk of infarction since it may rupture or tear away, blocking an artery or causing thrombosis, whereas the fibrous plaque is more stable and considered low risk. Macrophages are associated with plaque development. If macrophages or other cells are stimulated in a loose plaque, this can lead to fibrosis and deposition of fibrin and connective tissue, converting it to a fibrous plaque. Macrophages readily ingest particles, so metal particles may be used to accumulate them within the macrophage cytoplasm. Other lipoprotein particles are also ingested, and coating the metal particles with such substances can enhance delivery. Once loaded, the macrophages can be stimulated, damaged, or killed by external energy that is absorbed by the metal particles, such as x-rays or gamma rays, ultrasound, diathermy, or other sources. This stimulus can then start the natural response process of fibrosis, thus substantially reducing the risk and incidence of heart attack and stroke.

Targeting metal particles to plaque or plaque-associated cells may also be done by the other means described, such as use of antibodies, peptides, ligands, or other selectively binding moieties. Similarly, metallocytes may be localized in the region of interest.

Due to the disruption caused by the metal-radiation approach, plaques can be directly thinned or potentially removed altogether in a microscopic way. This approach would not carry the risk of the commonly used invasive procedures of balloon angioplasty, coronary artery bypass graft surgery, or laser angioplasty. The cost should also be substantially less.

Kidney Disease

Damage to the kidneys can occur by a number of routes, including infection, high blood pressure, high blood sugar, and autoimmune attack. Loss of kidney function usually involves damage to the nephrons and is also accompanied by replacement of normal tissue with scar tissue and fibrin deposits. Since fibrosis and other degenerative processes involve certain cells, such as response by mesangial cells and basement membrane tissue, these may be targeted and destroyed to inhibit the progression to end stage renal failure. The present invention targets metal particles to such cells, by the means described above, and external energy applied to eliminate some or all of them, thus blocking the cells' deleterious response. By blocking fibrosis, for example, normal tissue could be spared.

Alzheimer's Disease

The strategy for control of AD is to target the neurofibrillary tangles and/or senile plaques with metal particles. This may be done via the means described, such as use of antibodies or other targeting moieties. Next, external energy is applied as described previously, which can be x-rays, microwaves, ultrasound or other forms. This will cause disruption selectively in the region around the metal particles, and may be used to kill the defective cells overproducing the damaging proteins. In this way the progression of the disease may be slowed or stopped.

Obesity

One-fourth of the American population is overweight, posing not only cosmetic concern, but greatly increasing health risks of heart disease, stroke, diabetes, and cancer. Obviously, the current treatments have shortcomings: drugs have side effects and are expensive, diets are difficult to maintain, and liposuction is expensive and only partially effective.

The present invention may be used to treat obesity. One embodiment is to coat gold particles with lipids, or other materials that preferentially target adipocytes. The particles will then be ingested and accumulate in adipose tissue. Next, the patient is exposed to an external source of energy, for example ultrasound or x-irradiation. The gold particle-containing fat cells will be selectively killed.

This strategy has several important advantages: Dieting is lengthy, difficult, and does not eliminate proliferated fat cells; by contrast the treatment with metal particles followed by energy is rapid, requires no will power, and actually destroys proliferated fat cells, so the benefits will be more lasting. Although more similar to a drug treatment, the effect may be localized by the local application of energy and the metal targeting, so fewer systemic side effects should result.

Tuberculosis

Although antibiotics are the mainstay of therapy for TB, increasing drug resistance, and the continued high death rate, mandate that new and effective therapies be developed.

The present invention may be used to effect a new therapy. A preferred embodiment is to target infected lung macrophages with metal particles (for example, gold particles). It is known that macrophages have high phagocytic activity and typically engulf particulates. The gold particles may be administered in an aerosol, and may be coated with an appropriate substance to enhance phagocytosis by the macrophages. Once internalized, the gold particles accumulate in lysosomes and endosomes and are not ejected. In this way, multiple doses can be used to increase the amount of gold particles in the target macrophages. When sufficient amounts are reached, the patient will be subjected to external energy, such as x-irradiation. The gold particles will intensify the deposition of energy in the macrophages compared to normal tissue, and selectively kill both the infected macrophages and coexisting bacteria.

Malaria

Since about 300 million people are infected and 1.5 million people die of malaria per year, and increasing resistance to the drugs used for treatment has been documented, it is clear that new and effective therapies are necessary but not obvious, or they would have been implemented.

The general method described in this specification are applicable to a completely new therapy for malaria. More specifically, during part of the life cycle of the protozoan parasite Plasmodium, a population of red blood cells in the host are infected, and the parasite feeds on the hemoglobin. These infected red cells may be recognized immunologically, or based on their surface charge changes, or other alterations. Based upon such identifying characteristics, metal particles may be targeted to the infected cells, for example by using an antibody. Subsequent x-irradiation (or other forms of external energy application, as described) may be applied to specifically damage the Plasmodium organisms.

Other Diseases and Conditions

To one skilled in the art, it should be clear from the information provided in this disclosure, how one might logically apply the invention to deliver metal particles to cells or sites of concern, then use excitation energy to effect cytotoxicity or other morphological changes. Many other diseases and medical conditions should be amenable to the approach described with minor adaptations.

Imaging

Imaging or detection either for diagnosis or material examination is enhanced by imaging contrast agents. Metal particles satisfy the requirements for effective imaging agents for many modalities, due to their very different properties from animal tissue or many other materials. Use of metal particles alone, attached to antibodies or other moieties, or highly loaded cells or synthetic vesicles may greatly improve visibility. The use of the latter, highly loaded metallocytes may greatly improve visibility compared to small molecules that carry only small amounts of imaging agents. An increase in sensitivity would be of importance for earlier detection of tumors, for example. Furthermore, targeting of metal particle loaded vesicles to sites of interest would also enable specific detection. Metal particles should be useful for imaging or detection by gamma and x-rays, using absorbtion or induced x-ray fluorescence, computed tomography (CAT), ultrasound, magnetic resonance imaging (MRI), light, light microscopy, electron microscopy, and many other forms of imaging or detection.

EXAMPLES

1. Preparation of Gold or Silver Loaded Erythrocytes.

Human blood was centrifuged at low speed to isolate red cells. These were then washed in phosphate buffered saline, pH 7.4 (PBS) and centrifuged again. 50 microliters of packed red cells were then hypotonically lysed in 1 ml of cold 5 mM phosphate, pH 8 buffer containing 10 micromolar magnesium sulfate and either ~1 O.D. (optical density at 525 nm, final) of 20 nm colloidal gold, or 20–200 nmoles of gold clusters (typically 1.4 nm,gold diameter).

After lysis, cell membranes were spun at 4,000×g. for 2 minutes in a 1.5 ml polyethylene tube to pellet the membranes. The supernatant was removed and the pellet warmed to 37 degrees C. to reduce the size of the lytic pore. In some cases, the salt concentration (NaCl) was adjusted to 0.2 Molar for further pore reduction. After 5–15 min. the cell membranes were washed by resuspension in 1 ml of PBS, centrifuged at 4,000×g. for 2 min, and repeating this resuspension and centrifugation 3 times.

The pellet was then resuspended in an autometallographic developer solution containing silver or gold ions. Within a few minutes the solution turned dark purple or black, and upon examination in the light microscope, metal deposition was found to be confined to within the cell membranes. The metal containing cells were washed by slow speed centrifugation, or just allowed to settle. Examination in an electron microscope revealed dense packing of large metal particles largely filling the cell volume.

2. Preparation of Small Cell Membrane Vesicles Loaded with Gold or Silver.

The protocol was the same as given in example 1, except that after cell lysis, the ghost membranes were homogenized by multiple passages through a 27 gauge needle. Also, a higher speed centrifugation was used to collect the smaller membrane vesicles, namely 15,000×g. for 3 min. Microscopic investigation revealed small vesicles approximately 0.02 to 4 microns in size depending on amount of homogenization. The vesicles were intensely light absorbing and shown to contain dense packing of metal particles.

3. Preparation of Metal Particle Vesicles Using Detergent.

Protocol was the same as in example 1, except that 0.1%. saponin was used to create holes in the cell membrane instead of hypotonic lysis. Lytic holes were reduced in size by removing the detergent from the buffer.

4. Preparation of Gold Containing Cell Vesicles Using Covalent Coupling of Seed Gold to Inside of Cell Membranes.

50 microliters of washed red blood cells were reacted with N-ethyl maleimide to block thiols on their outside surface. After hypotonic lysis in 5 mM phosphate, pH 8 with 10 micromolar Mg sulfate, the ghosts were reacted with 20 nmoles maleimido Nanogold, a 1.4 nm gold cluster that covalently reacts and binds to thiols. Since the outer surface thiols had been blocked, this targeted the nucleating small gold clusters to the inner surface of the membranes. After reaction for 2 hrs, the membranes were washed as in example 1 and enhanced with the gold or silver developer. Dense internal loading of the vesicles was observed, but many of them had become smaller than the original cell size during this procedure.

5. Targeting of Metal Containing Cell Vesicles.

Gold containing erythrocytes (here termed "Aurocytes") were prepared as given in example 1. Goat anti-mouse IgG was coupled to the aurocytes by suspending them in a 150 mM NaCl solution with the antibody concentration adjusted to 0.1 mg/ml. A 0.01% solution of chromic chloride (pH adjusted to 5) was added with vortexing, the amount just equal to what causes agglutination of red cells that have no antibody added. After a few minutes the aurocytes were purified by centrifugation. A test target was prepared by spotting 1 microliter of mouse IgG on nitrocellulose, drying, and blocking with 4% bovine serum albumen. The IgG-aurocytes were applied in PBS and agitated. Within about 10 min nearly all the gold containing cells (aurocytes) were found on the target area, which became black.

6. Microwave Heating of Silver Particles.

Silver particles in water were prepared by silver development of 20 nm colloidal gold. This was placed in a conventional microwave, and irradiated for 5–30 sec. Boiling of the solution occurred more rapidly than control tubes only containing water, and positioned at the same place inside the microwave oven to control for intensity variations.

7. Cell Damage Caused by Metal Particles with Ultrasound.

Gold containing erythrocyte membranes (Aurocytes) were prepared as described in example 1. These were mixed in suspension with a human cell culture line that was harvested by a brief trypsin exposure to get them in suspension. A microtip sonicator was inserted and pulsed on for 15 sec at a low level. At the end of the treatment, light microscopy revealed that all cells were disrupted. Control suspensions sonicated at the same level without the aurocytes survived without disruption, as did cells and aurocytes without sonication.

8. Accumulation of Gold Particles within Cells by Receptor Mediated Endocytosis.

A human brain cancer cell line, A431, that overexpresses the epidermal growth factor receptor (EGFr) was grown in vitro, while having in the medium 10 nm gold particles conjugated to monoclonal anti-EGFr antibodies. After two days, cell survival was identical to untreated cells, indicating no apparent toxicity, but the cells became blue-black in color, due to the internal accumulation and aggregation of gold particles. 10 nm gold particles, normally red in color, are known to change to blue-black when aggregated or concentrated so the particles are within close proximity. Fixation of cells and development with a silver enhancer caused the cells to become very dark by bright field light microscopy, and become highly visible by epi-illumination reflection microscopy. A control cell line that is known to have little EGFr, MCF7 cells, did not become colored or silver enhanced when subjected to the same conditions.

9. Specific Cell Death of Human Tumor Cells Caused by Targeting of Gold Particles Followed by x-Irradiation.

A431 cells were grown in the presence of 10 nm gold particles conjugated to anti-EGFr antibodies for two days, as described in Example 8, harvested, washed, and aliquoted into tubes. Cells and controls were irradiated with x-rays from a clinical x-ray machine at doses of 0, 2, 4, 8, and 10 Gray. A standard clonogenic assay revealed that cell survival was dramatically reduced for the tumor cells expressing EGFr that were exposed to the gold particle-anti-EGFr antibody conjugate, compared to control cells which had no gold uptake.

Conclusion, Ramifications, and Scope

The present invention can be used to enhance therapies as well as imaging contrast. Delivery of metal particles to sites of interest followed by application of various forms of energy or radiation can be tailored in a number of ways to kill specific cells, ablate unwanted tissue, stimulate physiological responses, and for imaging, provide highly absorptive or secondary emissive material that increases the sensitivity of detection. High loading of cells, cell membrane vesicles, cell membrane fragment vesicles, or synthetic vesicles with metal particles can greatly increase the intended effects by delivering higher amounts of metal to the target region.

Furthermore, the invention has the additional advantages:

effects of the metal particle and radiation are highly localized, since they are a combination of two processes: a) localization of the metal particles and b) application of the radiation to a confined region. This overcomes a significant drawback of many other therapies, such as chemotherapy, that are administered systemically and produce serious side effects and toxicities in non-target organs.

radiotherapy is enhanced and more effective, since the dose is increased by the metal particles to the target tissue, thus sparing normal tissue. This means that higher, lethal doses can be selectively delivered to tumor cells.

therapy with metal particles combined with radiation has advantages over surgery in that cellular targeting is possible, thus enabling finer resolution of tissue treatment than possible with surgery, especially valuable when surgery is not possible, or in combination with surgery to remove all target cells. Less invasiveness and lower risk may be achieved with metal-radiation therapy than with many surgical procedures.

standard and common x-ray and gamma-ray sources can be used, an advantage over other novel therapies that require extensive new equipment, such as boron neutron capture therapy that may require a nuclear reactor delivery of metal particles is versatile since they can be combined with many known directing moieties, such as antibodies, peptides, drugs, proteins, lipids, lectins, carbohydrates, nucleic acids, and other materials. This is an advantage over most drugs or other substances which not only must be therapeutic, but target the region or cell type to be treated. By separating these two functions, the therapeutic (from the irradiation) and the targeting (by the attached antibody or other moiety), a more efficient and rational delivery may be achieved than with one compound that must serve both functions.

receptor mediated endocytosis may be used effectively to accumulate therapeutic amounts of metal in target cells over a period of time. This is not possible with many drugs or other substances that diffuse out of the target cell (whereas the metal particles do not) even if endocytosed. This allows a powerful new therapeutic process.

destruction of angiogenic endothelium by the invented process has several advantages over other anti-angiogenic therapies which miss important cells at the tumor periphery, must be continuously administered, and may not effectively block all angiogenic agonists.

effective range of the secondary emissions from the metal particles can be controlled by energy of the exciting beam, thus allowing external control of the effects. This is not possible with many other therapies.

a variety of energy sources can be used to render different desired effects. For example, x-radiation, gamma radiation, proton beam, particle beams, diathermy, microwaves, alternating current, radio frequencies, light, sound and ultrasound may be used. Each of these interacts with the metal particles differently, producing different effects and ranges of effects that are useful for therapies and imaging.

intervention of heart disease, stroke, atherosclerosis, kidney disease, Alzheimer's disease, obesity, *tuberculosis*, malaria, and other conditions are possible with the invention in ways not currently available. The course of these diseases may be significantly altered by metal particle and applied energy or radiation therapy.

directed metal particle localization provides improved and higher resolution imaging.

metal-loaded cells or vesicles that can be targeted by directing moieties attached, greatly enhance metal-radiation effects by delivering greater quantities and concentration of metal to the desired sites.

The present invention may be applied to areas outside of medical treatment and diagnosis, for example, the microscopic targeting of charged metal particles to oppositely written charged patterns, followed by radiation exposure to alter the matrix, thus providing a novel method of nanofabrication.

Although the description contains many examples and specifics, these should not be construed as limiting the scope of the invention, but as merely providing illustrations of some of the presently preferred embodiments.

I claim:

1. A method for loading metal particles into erythrocyte membrane vesicles, comprising the steps, in the following order:
   a) providing erythrocytes in a solution containing metal nucleating particles which have a catalytic surface suitable for metal ion deposition;
   b) treating the erythrocytes to produce an opening in the surface membrane of the erythrocytes to allow passive loading of the metal nucleating particles, thereby producing erythrocyte membrane vesicles which contain the metal nucleating particles;
   c) treating the erythrocyte membrane vesicles to reduce the size of the opening produced in step b) to allow retention of the metal nucleating particles within the erythrocyte membrane vesicles;
   d) washing the erythrocyte membrane vesicles to remove extracellular metal nucleating particles; and
   e) treating the erythrocyte membrane vesicles to catalytically deposit metal by diffusing metal ions in combination with a reducing agent through openings of step c), whereby the reducing agent acts to catalytically reduce the metal ion to form an insoluble metal which is immobilized internally around the nucleating small metal particles within the erythrocyte membrane vesicles thereby producing metal particles which occupy more than 10% of the erythrocyte membrane vesicle internal volume.

2. A method for loading metal particles into erythrocyte membrane vesicles, comprising:
   a) providing erythrocytes;
   b) washing the erythrocytes in physiologically buffered solution;
   c) lysing the washed erythrocytes hypotonically in a solution containing from 20 to 200 $\mu$Molar metal nucleating particles which have a catalytic surface suitable for metal ion deposition, thereby producing erythrocyte membrane vesicles which contain the metal nucleating particles;
   d) incubating the erythrocyte membrane vesicles of step c) at 37° C. for between 5 and 15 minutes;
   e) washing the incubated erythrocyte membrane vesicles of step d) with physiologically buffered solution, to remove extracellular metal nucleating particles; and
   f) treating the washed erythrocyte membrane vesicles of step e) to catalytically deposit metal by diffusing metal ions in combination with a reducing agent into the erythrocyte membrane vesicles of step c) whereby the reducing agent acts to catalytically reduce the metal ion to form an insoluble metal which is immobilized internally around the nucleating small metal particles within the erythrocyte membrane vesicles to produce metal particles which occupy more than 10% of the erythrocyte membrane vesicle internal volume.

3. The method of claim 2 wherein the physiologically buffered solution is phosphate buffered saline (pH 7.4).

4. The method of claim 2 wherein lysing step c) occurs in a solution of 5 mM phosphate buffer (pH 8), containing 10 $\mu$M magnesium sulfate.

5. The method of claim 2 wherein the metal ions are selected from the group consisting of gold, silver, nickel, copper, cobalt, alloys, platinum, and palladium.

6. The method of claim 2 wherein the erythrocytes are human erythrocytes.

7. The method of claim 2 wherein the metal nucleating particles are gold clusters or gold colloids.

8. The method of claim 2 further comprising the addition of NaCl to the erythrocyte membrane vesicles to a final concentration of 0.2 M, after lysing step c), prior to incubating step d).

9. The method of claim 2 further comprising washing the membrane vesicles which contain metal particles produced in step f) with physiologically buffered solution.

10. A method for loading metal particles into erythrocyte membrane vesicles, comprising:
    a) providing erythrocytes;
    b) washing the erythrocytes in physiologically buffered solution;
    c) lysing the washed erythrocytes in a physiologically buffered solution containing a detergent, and from 20 to 200 $\mu$Molar metal nucleating particles which have a catalytic surface suitable for metal ion deposition, thereby producing erythrocyte membrane vesicles which contain metal nucleating particles;
    d) washing the erythrocyte membrane vesicles produced in step c) with physiologically buffered solution, to remove extracellular metal nucleating particles; and
    e) treating the washed erythrocyte membrane vesicles of step d) to catalytically deposit metal by diffusing metal ions in combination with a reducing agent into the erythrocyte membrane vesicles of step c) whereby the reducing agent acts to catalytically reduce the metal ion to form an insoluble metal which is immobilized internally around the nucleating small metal particles within the erythrocyte membrane vesicles to produce metal particles which occupy more than 10% of the erythrocyte membrane vesicle internal volume.

11. The method of claim 10 wherein the detergent of step c) is saponin.

12. The method of claim 10 wherein the detergent of step c) is 0.1% saponin.

13. The method of claim 10 wherein the physiologically buffered solution is phosphate buffered saline (pH 7.4).

14. The method of claim 10 wherein the erythrocytes are human erythrocytes.

15. The method of claim 10 wherein the metal ions are selected from the group consisting of gold, silver, nickel, copper, cobalt, alloys, platinum, and palladium.

16. The method of claim 10 wherein the metal nucleating particles are gold clusters or gold colloids.

17. The method of claim 10 further comprising washing the erythrocyte membrane vesicles which contain metal particles of step e) in physiologically buffered solution.

18. A method for loading metal particles into erythrocyte membrane fragment vesicles, comprising:
   a) providing erythrocytes;
   b) washing the erythrocyte in physiologically buffered solution;
   c) lysing the washed erythrocytes hypotonically in a solution containing from 20 to 200 $\mu$Molar metal nucleating particles which have a catalytic surface suitable for metal ion deposition, thereby producing erythrocyte membrane vesicles which contain the metal nucleating particles;
   d) homogenizing the erythrocyte membrane vesicles of step c) to produce small erythrocyte membrane vesicles from 0.02 $\mu$m to 4 $\mu$m in diameter;
   e) incubating the small erythrocyte membrane vesicles of step d) to 37° C. for between 5 and 15 minutes;
   f) washing the incubated erythrocyte membrane fragment vesicles of step e) with physiologically buffered solution, to remove extracellular metal nucleating particles; and
   g) treating the washed small erythrocyte membrane vesicles of step f) to catalytically deposit metal by diffusing metal ions in combination with a reducing agent into the erythrocyte membrane vesicles of step c) whereby the reducing agent acts to catalytically reduce the metal ion to form an insoluble metal which is immobilized internally around the nucleating small metal particles within the small erythrocyte membrane vesicles to produce metal particles which occupy more than 10% of the erythrocyte membrane vesicle internal volume.

19. The method of claim 18 wherein the physiologically buffered solution is phosphate buffered saline (pH 7.4).

20. The method of claim 18 wherein lysing step c) occurs in a solution of 5 mM phosphate buffer (pH 8), containing 10 $\mu$M magnesium sulfate.

21. The method of claim 18 wherein homogenizing step d) is by passage of the erythrocyte membrane vesicles through a 27 gauge needle.

22. The method of claim 18 wherein homogenizing step d) is by sonication of the erythrocyte membrane vesicles.

23. The method of claim 18 wherein the metal are selected from the group consisting of gold, silver, nickel, copper, cobalt, alloys, platinum, and palladium.

24. The method of claim 18 wherein the erythrocytes are human erythrocytes.

25. The method of claim 18 wherein the metal nucleating particles are gold clusters or gold colloids.

26. The method of claim 18 further comprising the addition of NaCl to the erythrocyte membrane vesicles to a final concentration of 0.2 M, after step c), prior to incubating step e).

27. The method of claim 18 further comprising washing the small erythrocyte membrane vesicles produced by step g) with physiologically buffered solution.

28. A method for loading metal particles into erythrocyte membrane vesicles, comprising:
   a) providing erythrocytes;
   b) washing the erythrocytes in physiologically buffered solution;
   c) lysing the washed erythrocytes in a physiologically buffered solution containing a detergent, and from 20 to 200 $\mu$Molar metal nucleating particles which have a catalytic surface suitable for metal ion deposition, thereby producing erythrocyte membrane vesicles which contain metal nucleating particles;
   d) homogenizing the erythrocyte membrane vesicles of step c) to produce small erythrocyte membrane vesicles from 0.02 $\mu$m to 4 $\mu$m in diameter, which contain metal nucleating particles;
   e) washing the small erythrocyte membrane vesicles of step d) with physiologically buffered solution, to remove extracellular metal nucleating particles; and
   f) treating the washed small erythrocyte membrane vesicles of step e) to catalytically deposit metal by diffusing metal ions in combination with a reducing agent into the erythrocyte membrane vesicles of step c) whereby the reducing agent acts to catalytically reduce the metal ion to form an insoluble metal which is immobilized internally around the nucleating small metal particles within the small erythrocyte membrane vesicles to produce metal particles which occupy more than 10% of the erythrocyte membrane vesicle internal volume.

29. The method of claim 28 wherein the physiologically buffered solution is phosphate buffered saline (pH 7.4).

30. The method of claim 28 wherein the detergent of step c) is saponin.

31. The method of claim 28 wherein the detergent of step c) is 0.1% saponin.

32. The method of claim 28 wherein homogenizing step c) is by passage of the erythrocyte membrane vesicles through a 27 gauge needle.

33. The method of claim 28 wherein homogenizing step d) is by sonication of the erythrocyte membrane vesicles.

34. The method of claim 28 wherein the metal are selected from the group consisting of gold, silver, nickel, copper, cobalt, alloys, platinum, and palladium.

35. The method of claim 28 wherein the erythrocytes are human erythrocytes.

36. The method of claim 28 wherein the metal nucleating particles are gold clusters or gold colloids.

37. The method of claim 28 further comprising washing the small erythrocyte membrane vesicles produced by step h) with physiologically buffered solution.

38. The method of claim 1 wherein treating step e) is performed by suspending the erythrocyte membrane vesicles in a solution comprising a reducing agent and the metal ions.

39. The method of claim 2 wherein treating step f) is performed by suspending the washed erythrocyte membrane vesicles in a solution comprising a reducing agent and the metal ions.

40. The method of claim 10 wherein treating step e) is performed by suspending the washed erythrocyte membrane vesicles in a solution comprising a reducing agent and the metal ions.

41. The method of claim 18 wherein treating step g) is performed by suspending the washed small erythrocyte membrane vesicles in a solution comprising a reducing agent and the metal ions.

42. The method of claim 28 wherein treating step f) is performed by suspending the washed small erythrocyte membrane vesicles in a solution comprising a reducing agent and the metal ions.

43. The method of claim 2, wherein the metal nucleating particles are 1.4 nm in diameter.

* * * * *

UNITED STATES PATENT AND TRADEMARK OFFICE
CERTIFICATE OF CORRECTION

PATENT NO.    : 6,645,464 B1
DATED         : November 11, 2003
INVENTOR(S)   : James F. Hainfeld It is certified that error appears in the above-identified patent and that said Letters Patent is hereby corrected as shown below:

Column 26,
Line 10, delete "buffered'solution," and substitute therefore -- buffered solution, --.

Signed and Sealed this

Thirteenth Day of January, 2004

JON W. DUDAS
*Acting Director of the United States Patent and Trademark Office*